(12) United States Patent
Hojo et al.

(10) Patent No.: US 8,834,910 B2
(45) Date of Patent: Sep. 16, 2014

(54) SUSTAINED RELEASE DISPENSER COMPRISING TWO OR MORE SEX PHEROMONE SUBSTANCES

(75) Inventors: Tatsuya Hojo, Niigata-ken (JP); Kinya Ogawa, Tokyo (JP); Noboru Aiba, Niigata-ken (JP); Takehiko Fukumoto, Niigata-ken (JP)

(73) Assignee: Shin-Etsu Chemical Co., Ltd. (JP)

( * ) Notice: Subject to any disclaimer, the term of this patent is extended or adjusted under 35 U.S.C. 154(b) by 130 days.

(21) Appl. No.: 10/801,229

(22) Filed: Mar. 16, 2004

(65) Prior Publication Data
US 2004/0185080 A1   Sep. 23, 2004

(30) Foreign Application Priority Data
Mar. 17, 2003   (JP) .................... 2003-071168

(51) Int. Cl.
*A01N 25/34* (2006.01)
*A01N 31/02* (2006.01)
*A01N 37/02* (2006.01)
*A01M 1/20* (2006.01)
*A01N 25/18* (2006.01)
*A01N 35/02* (2006.01)

(52) U.S. Cl.
CPC ............. *A01N 31/02* (2013.01); *A01N 37/02* (2013.01); *A01M 1/2044* (2013.01); *A01N 25/18* (2013.01); *A01N 35/02* (2013.01)
USPC ............ 424/412; 424/405; 424/409; 424/411

(58) Field of Classification Search
USPC .................. 424/405, 409, 411, 412
See application file for complete search history.

(56) References Cited

U.S. PATENT DOCUMENTS

| | | | |
|---|---|---|---|
| 4,017,030 A | 4/1977 | Coplan et al. ........... 239/44 |
| 4,600,146 A | 7/1986 | Ohno .................... 239/6 |
| 4,734,281 A | 3/1988 | Yamamoto et al. | |
| 5,002,971 A | 3/1991 | Becker et al. | |
| 5,278,141 A * | 1/1994 | Berliner ............ 512/3 |
| 6,355,236 B2 | 3/2002 | Ishino et al. | |
| 6,419,943 B1 | 7/2002 | Sakurada et al. ......... 424/411 |
| 6,594,947 B2 * | 7/2003 | Lingren et al. ........... 43/114 |
| 6,599,500 B1 | 7/2003 | Ogawa et al. | |
| 6,806,293 B1 | 10/2004 | Zamir | |
| 2005/0235400 A1 * | 10/2005 | Campbell et al. ........ 2/406 |

FOREIGN PATENT DOCUMENTS

| | | | | |
|---|---|---|---|---|
| DE | 2641630 A1 | 8/1977 | ........... A01M 13/00 |
| EP | 0243007 | 10/1987 | |
| EP | 0342126 A2 | 11/1989 | ........... A01N 25/18 |
| EP | 0540932 * | 5/1993 | |
| EP | 540932 A1 * | 5/1993 | |
| EP | 0540932 A1 | 5/1993 | ........... A01N 25/18 |
| EP | 0913088 A1 | 5/1999 | ........... A01M 1/20 |
| EP | 0938842 | 9/1999 | |
| EP | 0938842 A1 | 9/1999 | ........... A01N 25/18 |
| JP | 61-185445 A | 8/1986 | |
| JP | 62-198201 | 9/1987 | |
| JP | 02-069902 | 3/1990 | |
| WO | WO88/03755 | 6/1988 | |

OTHER PUBLICATIONS

European Search Report, corresponding to Application EP04101052.1, mailed Jul. 28, 2004.
Japanese Official Action for corresponding application No. 2003-071168, dated Jul. 30, 2009.
Aukrust et al. The Synthesis of (Z)-8-Dodecen-1-ol and its Acetate, Pheromone Components of the Oriental Fruit Moth (*Grapholita molesta*), Acta Chemica Scandinavica B 39:267-272 (1985).
Official Action corresponding to Japanese Patent Application No. 2003-71168 mailed Mar. 13, 2012.
Office Action corresponding to Japanese Patent Application No. 2010-259965 mailed Apr. 5, 2013.
European Search Report corresponding to application No. EP 05110016.2-2013 dated Mar. 18, 2006.
Methyl Myristate, Sigma Aldrich, online, http://www.sigmaaldrich.com/catalog/ProductDetail.do?N4=W272205|ALDRICH&N5=Product%20No.|Brand_Key&F=SPEC, 2 pages, Accessed Dec. 18, 2008.
Ethyl Myristate, Sigma Aldrich, online, http://www.sigmaaldrich.com/catalog/ProductDetail.do?N4=W272203|ALDRICH&N5=Product%20No.|Brand_Key&F=SPEC, 2 pages, Accessed Dec. 18, 2008.
Methyl Palmitate, Sigma Aldrich, online, http://www.sigmaaldrich.com/catalog/ProductDetail.do?N4=46235|RIEDEL&N5=Product%20No.|Brand_Key&F=SPEC, 1 page, Accessed Dec. 18, 2008.
Ethyl palmitate, Sigma Aldrich, online, http://www.sigmaaldrich.com/catalog/ProductDetail.do?N4=W245100|ALDRICH&N5=Product%20No.|Brand_Key&F=SPEC, 2 pages, Accessed Dec. 18, 2008.
Pyatnova et al., "Pheromone Composition for Disorientation of Oriental and Plum Moths", STN Database Accession No. 2002:741452 (2002).

* cited by examiner

*Primary Examiner* — Ali Soroush
(74) *Attorney, Agent, or Firm* — Myers Bigel Sibley & Sajovec, P.A.

(57) ABSTRACT

Provided are a sustained release dispenser which can control the release of sex pheromone simultaneously toward two or more species of insect pests and can also release the sex pheromone in response to the generation period of insect pest and the pest control method toward two or more insect pests. Provided specifically is a sex pheromone sustained release dispenser comprising two or more sex pheromone substances, each substance being aliphatic derivative having 10 to 20 carbons, and first and second chambers wherein some or all of the sex pheromone substance having a smallest carbon number excluding a carbon number in a functional group is contained in a first polymer chamber and the remainder is contained in a second polymer chamber. Provided also is a pest control method for using the sex pheromone sustained release dispenser.

5 Claims, 1 Drawing Sheet

SUSTAINED RELEASE DISPENSER COMPRISING TWO OR MORE SEX PHEROMONE SUBSTANCES

RELATED APPLICATION

This application claims priority from Japanese Patent Application No. 2003-071168 filed Mar. 17, 2003, the disclosure of which is incorporated by reference herein in its entirety.

BACKGROUND OF THE INVENTION

1. Field of the Invention

The invention relates to a sustained release dispenser as well as a pest control method, enabling a simultaneous release of two or more sex pheromone substances.

2. Description of the Related Art

As an effective method for utilizing a sex pheromone of an insect pest, the method has progressed to a practical stage, where a certain concentration of chemically synthesized sex pheromone is kept in a field so as to disrupt the mating of the insect pest. The important issues for the pest control method are development of the sustained release formulation (or dispenser) which can discharge a synthesized sex pheromone substance of an insect pest at a certain rate or higher in a long period; and the period of the mating disruption toward a target insect pest.

There are many cases where it is relatively easy to control the release of one or more sex pheromone substances of a single species of insect pest at a certain rate in a certain period because said one or more sex pheromone substances are only one kind or two or more substances having similar chemical structures. However, it is difficult to enclose sex pheromone substances with very different chemical structures in one dispenser and then control the release of the substances toward an insect pest having the substances. For instance, a diamondback moth (*Plutella xylostella*), an insect harmful to vegetables, has the sex pheromone substances (Z)-1'-hexadecenal and (Z)-hexadecenyl acetate; and the beet armyworm (*Spodoptera exigua* (*Hubner*)(*Lepidoptera: Noctudae*)), an insect harmful to vegetables, has the sex pheromone substances (Z, E)-9, 12-tetradecenyl acetate and (Z)-9-tetradecenol. Thus, each harmful insect has sex pheromone substances with different functional groups. Further, a principal component in the sex pheromone substance of leaf rollers, insects harmful to fruit trees and tea, is (Z)-11-tetradecenyl acetate and some of minor components therein are (Z)-9-dodecenyl acetate and 11-dodecenyl acetate. Thus, although the components have same functional groups, they have different carbon numbers. Hence, when the components are enclosed in a same dispenser, it is not possible to control the release of each component because of each component having different vapor pressure. It should be noted that there is rarely a single kind of insect pest for a certain crop. Thus, it is usually necessary to control two or more insect pests simultaneously in an area having various insect pests such as Japan.

The difficulties encountered when designing a sustained release dispenser which releases compounds having different chemical structures simultaneously are described below:
(1) The release of compounds cannot be controlled because of each compound having a different boiling point (vapor pressure) due to a different functional group thereof;
(2) The release of compounds cannot be controlled because of each compound having a different boiling point (vapor pressure) due to a different carbon number thereof, even when the functional group of each compound is identical;
(3) A dispenser comprising a porous support without a vapor barrier will release a compound having a higher vapor pressure faster even if an evaporation area is identical.

It is also difficult to design a sustained release dispenser toward two or more insects at the same because the generation period of each insect pest differs.

SUMMARY OF THE INVENTION

Thus, there are cases where sex pheromone substances having different chemical structures are mixed toward a single kind of insect pest or sex pheromone substances are mixed toward two or more insect pests. However, it is difficult to release the compounds in the same ratio as the composition ratio in the dispenser. It is also difficult to control the release of the compounds in response to the generation of each kind of insect pests.

For instance, it is generally believed to be necessary to control three kinds of insect pests, leaf rollers, *Grapholita molesta* and *Carposina niponensis* simultaneously for the pear in Japan. The principal component of sex pheromone substances for the leaf rollers is Z-11-tetradecenyl acetate having 14 carbons excluding the carbons of the ester group. The principal component of the sex pheromone substances of the oriental fruit moth (*Grapholita molesta*) is Z-8-dodecenyl acetate having 12 carbons excluding the carbons of the ester group. The principal component of the sex pheromone substances of the peach fruit moth (*Carposina niponensis*) is Z-13-icosen-10-one having 20 carbons excluding the carbon of the carbonyl group. Although the vapor pressure of Z-8-dodecenyl acetate of the *Grapholita molesta* sex pheromone substance is higher than the vapor pressures of sex pheromone substances of the other two insect pests, a long-term release of Z-8-dodecenyl acetate is desirable. It is because it is important to protect the late-maturing cultivars of autumn from the insect pests. A sustained release dispenser which can satisfy the above requirement has not yet been developed.

On the other hand, in order to disrupt the mating of two or more species of insect pests, it is considered to design a dispenser for each type of insect pest sex pheromone substance and then place each individual dispenser to release the sex pheromone substance at different period in response to the generation of the insect. However, it requires high cost for the preparation of dispensers and large labor for the placements of dispensers. Consequently, it opposes to the present trend of laborsaving agriculture.

Thus, the development of a laborsaving sustained release dispenser which can release two or more sex pheromone substances in a desired manner has been anticipated.

The purpose of this invention is to provide a sustained release dispenser which can control the simultaneous release sex pheromone substances in case where the sex pheromone substances have different chemical structures of a single species of insect pest are mixed, and/or where the sex pheromone substances of two or more species of insect pests are mixed. In the latter case, the sustained release dispenser which can release the sex pheromone substances in response to the generation period of the insect pests are provided together with a pest control method.

The inventors studied for the sex pheromone dispensers which can solve the above problems, can control the simultaneous release of sex pheromone substances, and can release the sex pheromone substances in response to the generation period of the insect pests. Consequently, the inventors have found that a sustained release dispenser comprising some or all of the sex pheromone substance having the lowest carbon number excluding the carbon number of the functional group in one tube of polymer material, and the remainder of the sex pheromone substances in the other tube of polymer material is suitable for said purpose. It is preferable to bond these two tubes together in a parallel way and have them function as one unit. Then the invention is completed.

According to the present invention, a sex pheromone substance sustained release dispenser comprising at least two sex pheromone substances, each being aliphatic derivative having 10 to 20 carbons, and comprising first and second chambers of polymer materials wherein some or all of the sex pheromone substance having a lowest carbon number is in the first chamber and the remainder of the sex pheromone substances is in the second chamber. Also provided is a pest control method of using the sex pheromone substance sustained release dispenser. In addition, provided is a container for a sex pheromone substance sustained release dispenser comprising at least two sex pheromone substances of aliphatic derivatives each having 10 to 20 carbons and comprising first and second chambers of polymer materials, wherein some or all of the sex pheromone substance having a lowest carbon number is placed in the first chamber and the remainder of the sex pheromone substances is in the second chamber.

When the sustained release dispenser and the pest control method of this invention are used, it is possible to release sex pheromone substances simultaneously to control two or more insect pests, and to release sex pheromone substances in response to the generation periods of the insect pests.

DETAILED DESCRIPTION OF THE PREFERRED EMBODIMENTS

Figure 1:
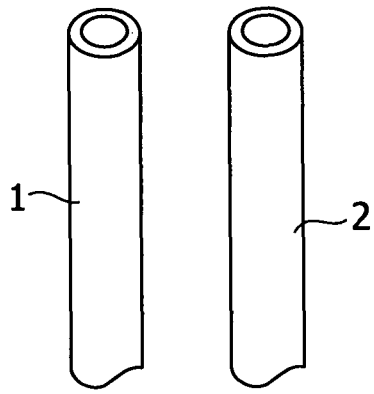
FIG. 1 illustrates the process of the sustained release dispenser of this invention, showing two tubes made of polymer material in FIG. 1(a), a joint in FIG. 1(b), the sealing process in which a heat sealing device is used in FIG. 1(c) and the cross section of the sustained release dispenser in Figure (d).
Figure 1:
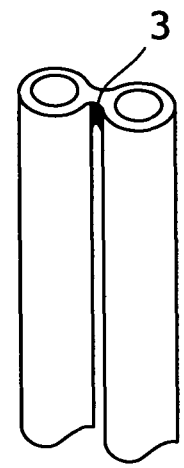
Figure 1:
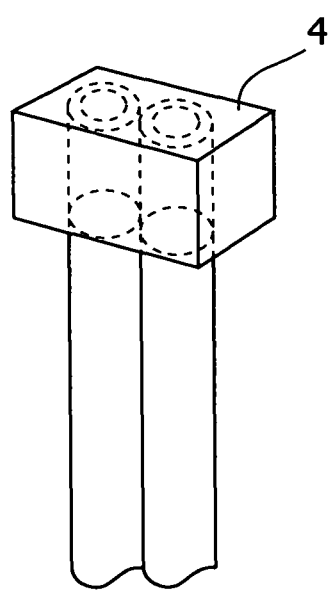
Figure 1:
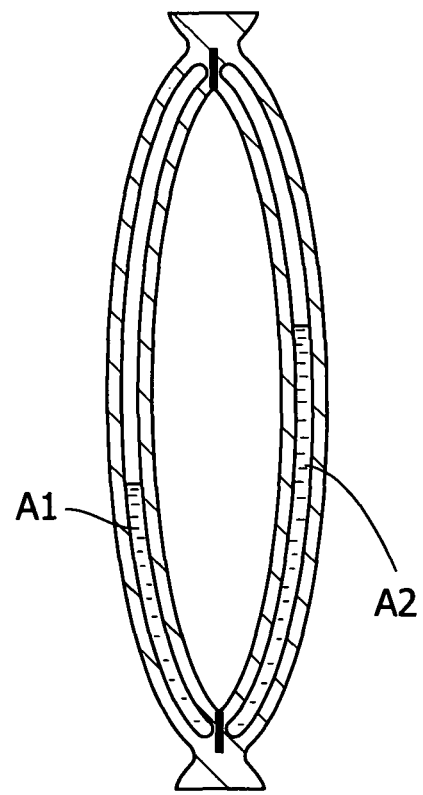

The invention will be explained in more detail below.

An example of sex pheromones toward insect pests is shown in Table 1. Chemical structure, relation with a target insect and carbon number of each component are listed in the pest control of the pear and peach in Japan. The vapor pressure was measured by the gas flow method at 25° C. according to the "Addendum to the OECD chemical test guideline, issues 7 and 8" (Adopted on Jul. 27, 1995).

TABLE 1

| Type of compound | Name of compound | Carbon number of Skelton | Biological activity | Vapor pressure (20° C.) (Pa) |
|---|---|---|---|---|
| Alcohol | Z-8-dodecene-1-ol | 12 | Minor component Of *Grapholita molesta* pheromone | 0.980 |
|  | Z-11-tetradecene-1-ol | 14 | Minor component Of leaf roller Pherone | 0.070 |
| Ester | Z-8-dodecenyl acetate | 12 | Main component of *Grapholita molesta* | 0.267 |
|  | Z-9-dodecenyl acetate | 12 | Minor component of leaf roller pheromone | 0.267 |
|  | 11-dodeceny acetate | 12 | Minor component of leaf roller pheromone | 0.246 |
|  | 10-methyldodecyl acetate | 13 | Minor component of leaf roller pheromone | 0.186 |
|  | Z-11-tetradecenyl acetate | 14 | Main component of leaf roller pheromone | 0.100 |
|  | Z-9-tetradecenyl acetate | 14 | Minor component of leaf roller pheromone | 0.100 |
| ketone | Z-13-icosen-10-one | 20 | Component of *Carposina niponensis* pheromone | 0.005 |

The above compounds are contained in a narrow tube, a capsule or a laminate of polymer material membrane and the release of the compounds are controlled by a barrier of the membrane. In this case, (1) vapor pressure of the enclosed sex pheromone substance and (2) affinity (solubility parameter) between the functional group of sex pheromone substance and the polymer material become important factors in the release control.

Because minor components in Table 1 are of small content, the main components are focused. It is considered that the difference in the affinity between each ester and the polymer material is extremely small and the difference between each ester and ketone is also relatively small. Thus, when a uniform solution containing all compounds in Table 1 is enclosed in a certain polymer material, the release rate of each component greatly depends on its vapor pressure. That is, esters having a higher vapor pressure such as 11-dodecenyl acetate, Z-8-dodecenyl acetate and Z-9-dodecenyl acetate will be released faster. Each of these compounds has 12 carbons excluding the carbon number of the functional group. On the other hand, compounds having a lower vapor pressure such as Z-11-tetradecenyl acetate and Z-13-icosen-10-one will be released slowly. Compounds which will be released faster cannot be released uniformly so that they result in shorter life time (effective release period) of a sustained release dispenser.

Hence, the inventors conducted various examinations and created a sustained release dispenser effective in cases when sex pheromone substances of a single species of insect pest having different chemical structures are mixed and/or when sex pheromone substances of two or more species of insect pests are mixed. The sustained release dispenser comprises first and second chambers of polymer materials, wherein some or all of mixture of the sex pheromone substances having a lowest carbon number (excluding the carbon number of the functional group) and having a high vapor pressure such as Z-8-dodecenyl acetate and Z-8-dodecene-1-ol in Table 1 is enclosed in the first chamber and the remainder of the sex pheromone substances is enclosed in the second chamber. It is preferable to bond the first and second chambers together in a parallel way so that they form one unit. Consequently, the pheromones do not suppress the release of the other pheromones. Therefore, the sex pheromone component of *Grapholita molesta* having the highest vapor pressure and the sex pheromone components of leaf rollers and *Carposina niponesis* can be released simultaneously in a long period. The invention is completed by this finding.

The sex pheromone substance used in the invention is an aliphatic derivative having 10 to 20 carbons. It preferably includes aliphatic linear alcohol of lepidopterans, and ester and ketone derived from the alcohol. Two or more of the sex pheromone substances are released simultaneously. The aliphatic derivative is preferably selected from the group consisting of an aliphatic linear alcohol having 10 to 18 carbons, an aliphatic linear acetate having 12 to 20 carbons and an aliphatic linear ketone having 10 to 20 carbons. It is noted that the carbon number of the functional group of the aliphatic linear acetate or aliphatic linear ketone is 1 or 2, respectively. Hence, when the carbon number of the functional group is excluded, the aliphatic linear acetate has 10 to 18 carbons and the aliphatic linear ketone has 9 to 19 carbons.

Two or more types of sex pheromone substances of the aliphatic derivative may be two or more sex pheromone substances in the category or two or more sex pheromone substances in the different categories. A stabilizer such as an antioxidant or UV absorber, or a colorant can be contained by 10% by weight or less in the sex pheromone substances.

As shown in Table 2, three species of insect pests are targeted in the case of the mating disruption agent toward insect pests of the pear and peach in Japan.

The *Grapholita molesta* have sex pheromone containing a main component of Z-8-dodecenyl acetate and a minor component of Z-8-dodecen-1-ol, and grows from the end of April to the end of September. The leaf rollers have sex pheromone containing a main component of Z-11-tetradecenyl acetate and minor components of Z-9-tetradecenyl acetate, Z-9-dodecenyl acetate, 11-dodecenyl acetate, 10-methyl dodecyl acetate and Z-11-tetradecen-1-ol, and grow from the middle of May to the beginning of September. The *Carposina niponensis* has sex pheromone containing a component of Z-13-icosen-10-one and grows from late May to the middle of September.

It should be noted that the main component refers to the highest content of sex pheromone component. The minor component refers to sex pheromone component or components other than the main component.

TABLE 2

| Name of insect pest | Growing period | Components of sex pheromone | Carbon number of skeleton | Vapor Pressure (20° C.) (Pa) |
|---|---|---|---|---|
| Grapholita Molesta | End of April to end of September | Z-8-dodecene-1-ol | 12 | 0.980 |
|  |  | Z-8-dodecenyl acetate* | 12 | 0.267 |
| Leaf roller | Middle of May to beginning of September | Z-9-dodecenyl acetate | 12 | 0.267 |
|  |  | 11-dodecenyl acetate | 12 | 0.246 |
|  |  | 10-methyldodecyl acetate | 13 | 0.186 |
|  |  | Z-11-tetradecenyl acetate* | 14 | 0.100 |
|  |  | Z-9-tetradecenyl acetate | 14 | 0.100 |
|  |  | Z-11-tetradecene-1-ol | 14 | 0.070 |
| Carposina niponensis | End of May to middle of September | Z-13-icosen-10-one* | 20 | 0.005 |

*The main component of natural sex pheromone for each insect pest is shown.

Some or all of the main component of the sex pheromone of *Grapholita molesta* which has the lowest carbon number is enclosed in a first independent polymer chamber, and the sex pheromones of *Carposina niponensis* and a leaf roller are enclosed in a second polymer chamber. A minor component of the sex pheromone of *Grapholita molesta* which has the same carbon number as the main component thereof may be enclosed in the second chamber. However, the minor component of the sex pheromone of *Grapholita molesta* is preferably enclosed in the second chamber together with the main component thereof because biological functions of minor components are often unknown.

The amount of sex pheromone substance or substances enclosed in each chamber is variable depending on the release period of the sustained release dispenser, the volatility of the sex pheromone substances, and the affinity or compatibility between the substances and polymer material for the container. The amount in the first chamber may be preferably 50 to 150 mg, more preferably 100 mg, and that in the second chamber may be preferably 200 to 300 mg, more preferably 230 mg.

The polymer material used in the invention may include polyolefin, acrylic, polyester, polyamide, methacrylic and copolymer of olefin and vinyl alcohol ester. When the membrane of the polymer material is used as a barrier, tube extruded in a general method, capsule, bag, and laminate may be included. Plasticizer, lubricant, stabilizer or colorant may be added in the processing stage. According to the invention, the polymer materials of the chambers or containers may be identical or different as long as they can be joined. The polymer materials of the chambers or containers may be preferably integrated to be one.

The shape of chamber or container made of polymer material is not limited as long as it can contain sex pheromone substance. For example, the sex pheromone substance may be contained in a narrow tube, capsule or laminate container, each comprising polymer membrane. The membrane can function as a barrier so that the release of the substance can be controlled.

The size of the polymer membrane can be selected in relation to the property of the contained sex pheromone substance. Thickness and the inside and outside diameters of the first and second chambers may be same or different. The thickness, in particular, is greatly influenced by the evaporation rate of the sex pheromone component so that the appropriate thickness can be selected in view of a necessary release period, a vapor pressure and solubility parameter of the sex pheromone component. It should be noted it is difficult to seal or joint the chambers containing the pheromone substance when the thickness of the first polymer chamber is extremely different from that of the second polymer chamber. Thus, the thickness has to be selected in practical range.

According to the invention, the construction of the first or second polymer chamber is not particularly limited. However, the construction which can be chemically connected by heat seal or adhesive may be preferable. Physical connection with tape or wire may be possible. Tube 1 of a first polymer chamber and tube 2 of a second polymer chamber may be separate as shown in FIG. 1(*a*), or joined at joint 3 in a parallel manner as shown in FIG. 1(*b*). It may be possible to connect the ends of two tubes together chemically or physically by using heat seal device 4 as shown in FIG. 1(*c*) so as to produce the dispenser comprising sex pheromones A1 and A2 as shown in the cross section of FIG. 1(*d*). It should be noted that the invention is not limited to the chamber constructions shown in figures.

This invention will be explained in detail in the following Examples and Comparative Examples, the use of which, however, is not limited to the following examples.

Example 1

Sustained release dispenser for controlling three insect species: *Grapholita molesta*, *Carposina niponensis* and leaf roller.

Dispensers in the form of 20-cm-long tubes (A) and (B) joined in a parallel manner as shown in FIG. 1 were prepared. The contents of tubes (A) and (B) are shown below. The dispensers were placed in 2 ha of a pear orchard in Chiba Prefecture, Japan, on May 9, as shown in Table 3. The dispensers were placed in ratio of 180 tubes per 10 a. As a result, damage caused by leaf roller, *Carposina niponensis* and *Grapholita molesta* was not observed in fruits up to harvest time of mid October. Residual percentages of each pheromone component of each species of insects for the tubes placed in the orchard are shown in FIG. 3.

(A) The following components were contained in a high-density polyethylene tube with inside diameter of 1.4 mm and outside diameter of 2.5 mm (tube thickness of 0.55 mm):

Leaf roller components

Z-11-tetradecenyl acetate: 88 mg

Z-9-tetradecenyl acetate: 17 mg 10-methyldodecyl acetate: 2 mg

Z-9-dodecenyl acetate: 5 mg 11-dodecenyl acetate: 2 mg

Z-11-tetradecene-1-ol: 1 mg

*Carposina niponensis* component

Z-13-icosene-10-one: 80 mg

*Grapholita molesta* components

Z-8-dodecenyl acetate: 34 mg

Z-8-dodecene-1-ol: 0.3 mg (B) The following components were contained in a high-density polyethylene tube with inside diameter of 0.90 mm and outside diameter of 2.30 mm (tube thickness of 0.70 mm)

*Grapholita molesta* components

Z-8-dodecenyl acetate: 95 mg

Z-8-dodecene-1-ol: 1 mg

TABLE 3

| | | Residual percentage (%) | | |
|---|---|---|---|---|
| Date | Elapsed days (day) | *Grapholita molesta* | Leaf roller | *Carposina niponensis* |
| May 9 | 0 | 100 | 100 | 100 |
| Jun. 8 | 30 | 68.9 | 85.7 | 94.7 |
| Jul. 6 | 58 | 45.9 | 71.2 | 88.3 |
| Aug. 8 | 91 | 16.1 | 45.2 | 73.9 |
| Sep. 6 | 120 | 8.2 | 26.3 | 53.4 |
| Oct. 6 | 150 | 4.8 | 17.2 | 44.1 |

Comparative Example 1

A 20-cm-long high-density polyethylene tube with inside diameter of 1.5 mm and outside diameter of 2.6 mm (thickness of 0.55 mm) was bonded with aluminum wire to afford it formability. The solution wherein all of the sex pheromone components used in Example 1 had been mixed uniformly was contained in the tube so as to produce the dispenser. Some of the dispensers were placed in said pear orchard. Changes of residual percentage of each pheromone component over elapsed time were measured.

The results are shown in Table 4 below.

TABLE 4

| | | Residual percentage (%) | | |
|---|---|---|---|---|
| Date | Elapsed days (day) | *Grapholita molesta* | Leaf roller | *Carposina niponensis* |
| May 9 | 0 | 100 | 100 | 100 |
| Jun. 8 | 30 | 51.9 | 89.5 | 96.2 |
| Jul. 6 | 58 | 25.1 | 79.2 | 89.1 |
| Aug. 8 | 91 | 2.9 | 55.3 | 80.2 |
| Sep. 6 | 120 | 2.3 | 45.3 | 75.4 |
| Oct. 6 | 150 | 1.1 | 27.5 | 59.3 |

According to the above results, the life time of the *Grapholita molesta* is believed to be about ninety days.

Example 2

The sex pheromone dispenser toward Peach Twig Borer (*Anarsia lineatella*) which is an insect pest of fruit trees outside of Japan comprises 20-cm-long tubes (A) and (B), joined in parallel manner as shown in FIG. 1, and the sex pheromone substance. The tubes (A) and (B) are described below. Release was confirmed at 0.3 m/s in a constant temperature tank at 25° C. Changes of the residual percentage of each sex pheromone component over elapsed days are shown in Table 5.

(A) The 140 mg of E-5-dodecenyl acetate is contained in a high-density polyethlene tube with inside diameter of 1.07 mm and outside diameter of 2.07 mm (thickness of 0.50 mm).

(B) The 60 mg of E-5-dodecenol is contained in a high-density polyethylene tube with inside diameter of 0.70 mm and outside diameter of 1.10 mm (thickness of 0.20 mm).

TABLE 5

| | Residual percentage (%) | | |
|---|---|---|---|
| Elapsed days (day) | Tube A E-5-dodecenyl acetate | Tube B E-5-dodecenol | A/B |
| 0 | 100 | 100 | 1.00 |
| 22 | 78.4 | 81.4 | 0.96 |

TABLE 5-continued

| | Residual percentage (%) | | |
|---|---|---|---|
| Elapsed days (day) | Tube A E-5-dodecenyl acetate | Tube B E-5-dodecenol | A/B |
| 55 | 45.8 | 48.3 | 0.95 |
| 85 | 23.9 | 26.0 | 0.92 |
| 111 | 9.1 | 10.3 | 0.88 |

Comparative Example 2

A 20-cm long high-density polyethylene tube with inside diameter of 1.28 mm and outside diameter of 2.48 mm (thickness of 0.60 mm) was bonded with aluminum wire to afford it formability. The solution wherein all of the sex pheromone components used in Example 2 had been mixed uniformly was contained in the tube so as to produce the dispenser. The dispensers were tested in the same manner as in Example 2. Changes of residual percentage of each pheromone component over elapsed time were measured.

TABLE 6

| | Residual percentage (%) | | |
|---|---|---|---|
| Elapsed days (day) | Tube A E-5-dodecenyl acetate | Tube B E-5-dodecenol | A/B |
| 0 | 100 | 100 | 1.00 |
| 22 | 83.2 | 96.0 | 0.87 |
| 55 | 49.2 | 75.6 | 0.65 |
| 85 | 28.7 | 57.9 | 0.50 |
| 111 | 16.0 | 44.5 | 0.36 |

The invention claimed is:

1. A sex pheromone sustained release dispenser comprising:

two or more sex pheromone substances, wherein each substance is an aliphatic derivative having 10 to 20 carbons, and a first and a second polymer chamber, wherein each chamber further comprises a polymer membrane, wherein some or all of the sex pheromone substance having a smallest carbon number excluding a carbon number in a functional group is contained in the first polymer chamber and any of the sex pheromone substance remaining is contained in the second polymer chamber, wherein the first and second polymer chambers and the polymer membrane of the chambers are made of the same material, wherein said material is polyolefin, and wherein the sex pheromone substances in the first and second polymer chambers are released at similar rates.

2. The sex pheromone sustained release dispenser according to claim 1 wherein said aliphatic derivative is selected from the group consisting of aliphatic linear alcohol having 10 to 18 carbons, aliphatic linear acetate having 12 to 20 carbons and aliphatic linear ketone having 10 to 20 carbons.

3. The sex pheromone sustained release dispenser according to claim 1 wherein said sex pheromone sustained release dispenser is for controlling two or more species of insect pests.

4. The sex pheromone sustained release dispenser according to claim 2 wherein said sex pheromone sustained release dispenser is for controlling two or more species of insect pests.

5. The sex pheromone sustained release dispenser according to claim 1, wherein: the sex pheromone substances are those for *Grapholita Molesta*, Leaf Roller and *Carposina niponesis*; some or all of a first mixture of Z-8-dodecenyl acetate and Z-8-dodecene 1-ol, which are sex pheromone substances for *Grapholita Molesta*, is contained in the first polymer chamber; and any remaining amount of the first mixture and a second mixture of Z-11-tetradecenyl acetate, Z-9-tetradecenyl acetate, Z-9-dodecenyl acetate, 11-dodecenyl acetate, 10-methyldodecyl acetate and Z-11-tetradecene-1-ol, which are sex pheromone substances for Leaf roller, and Z-13-icosen-10-one, which is a sex pheromone substance for *Carposina niponesis*, are contained in the second polymer chamber.

* * * * *